US012694978B2

(12) United States Patent
Preuhs et al.

(10) Patent No.: US 12,694,978 B2
(45) Date of Patent: Jul. 28, 2026

(54) METHOD FOR PROVIDING A PROCEDURAL SIGNAL, SYSTEM AND COMPUTER PROGRAM PRODUCT

(71) Applicant: Siemens Healthcare GmbH, Erlangen (DE)

(72) Inventors: Elisabeth Preuhs, Erlangen (DE); Markus Kowarschik, Erlangen (DE); Marcus Pfister, Bubenreuth (DE); Christian Kaethner, Freiburg (DE); Anne Tjorven Büssen, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 122 days.

(21) Appl. No.: 18/503,158

(22) Filed: Nov. 6, 2023

(65) Prior Publication Data

US 2024/0153628 A1 May 9, 2024

(30) Foreign Application Priority Data

Nov. 7, 2022 (DE) ..................... 10 2022 211 734.4

(51) Int. Cl.
G16H 40/67 (2018.01)
A61B 5/00 (2006.01)
(Continued)

(52) U.S. Cl.
CPC ........... *G16H 40/67* (2018.01); *A61B 5/0022* (2013.01); *A61B 5/7275* (2013.01); *G16H 20/10* (2018.01); *G16H 40/40* (2018.01)

(58) Field of Classification Search
CPC ........ G16H 40/67; G16H 20/10; G16H 40/40; G16H 20/40; G16H 40/63; A61B 5/0022; A61B 5/7275
See application file for complete search history.

(56) References Cited

U.S. PATENT DOCUMENTS 11,389,248 B1 7/2022 Roh et al.
2021/0393343 A1* 12/2021 Sankai .................. G06F 3/0346

FOREIGN PATENT DOCUMENTS

CN 113712674 A * 11/2021
EP 0201883 A2 11/1986

OTHER PUBLICATIONS

Zeng, Quan, et al. "A network communication protocols for robotic-assisted vascular intervention systems." 2017 2nd International Conference on Biological Sciences and Technology (BST 2017). Atlantis Press, 2018 (Year: 2018).*

(Continued)

*Primary Examiner* — Linh Giang Le
(74) *Attorney, Agent, or Firm* — Lempia Summerfield Katz LLC

(57) ABSTRACT

A method for providing a procedural signal includes receiving an item of procedural information including an item of information about at least one procedural step that has been carried out on an object under examination before the beginning of the method, and an item of information about at least one planned procedural step. A physiological patient parameter is received from the object, which has been acquired via a sensor unit during and/or subsequent to the procedural step that has been carried out. The method includes identifying, based on the patient parameter and/or a change in the patient parameter whether the at least one procedural step has been tolerated by the object under examination. A procedural signal is provided that, in the negative, includes an item of information for adapting the at least one planned procedural step based on the procedural information and, in the affirmative, includes approval of the at least one planned procedural step.

18 Claims, 4 Drawing Sheets

(51) Int. Cl.
G16H 20/10 (2018.01)
G16H 40/40 (2018.01)

(56) References Cited

OTHER PUBLICATIONS

"Endovascular Robotics: Building the future of robotics, imaging, and device integration," https://www.corindus.com/corpath-grx/how-it-works. (Screenshot: Oct. 20, 2023), pp. 1-4.
Workflow with CorPath GRX: YouTube video, Nov. 2, 2019, https://www.youtube.com/watch?v=p7UNJRoVNOw, pp. 1-2.

* cited by examiner

METHOD FOR PROVIDING A PROCEDURAL SIGNAL, SYSTEM AND COMPUTER PROGRAM PRODUCT

This application claims the benefit of German Patent Application No. DE 10 2022 211 734.4, filed Nov. 7, 2022, which is hereby incorporated by reference in its entirety.

BACKGROUND

The present embodiments relate to a method for providing a procedural signal, a system, and a computer program product.

In minimally invasive interventions, treatments (e.g., the placement of stents) or diagnoses (e.g., the detection of stenoses) are frequently carried out by medical objects introduced into the body. These medical objects are conventionally advanced to their deployment site using guide wires and catheters through an access in the groin (e.g., the femoral artery) or the left armpit (e.g., radial accesses via the subclavian artery). Navigation into the individual vessel branches frequently proceeds by rotating and advancing the guide wire or catheter at the entry point.

If such procedures are now assisted by a robotic movement apparatus (e.g., a catheter robot and/or a vascular navigation robot), the movement apparatus, remotely controlled by medical operating personnel (e.g., a physician) often takes over the manipulation of the medical object.

Depending on the application, the medical operating personnel may be in the same room as the movement apparatus or in an appropriate room in a remotely located hospital. In the second case, two people or groups often have to work together in "distributed" teams, local operating personnel at the same location as the object under examination and remote operating personnel for remotely controlling the movement apparatus. The remote operating personnel may also include just one person.

Use may be made of various aids to enable or assist communication between distributed teams during a remote procedure. For example, bidirectional real-time image transfer, additional information (e.g., about the medical instrument currently being used or its positioning), and vital parameters of the object under examination may be provided. Situations nevertheless remain in which the remote operating personnel's "limited perception" of the current local situation may have a negative impact on the examination or treatment. The remote operating personnel do not directly "experience" the procedure (e.g., a state or a response of the object under examination to specific procedural steps). As a result, procedural steps that, although reasonable and necessary based on the "transmitted data situation," prove to be contraindicated for the "direct patient experience" may be initiated. Contraindications of which neither team is aware may sometimes also occur. In an extreme case, such contraindicated procedural steps may be performed repeatedly because the remote operating personnel were unaware of the negative response of the object under examination on the first occasion the procedural step was performed.

SUMMARY AND DESCRIPTION

The scope of the present invention is defined solely by the appended claims and is not affected to any degree by the statements within this summary.

The present embodiments may obviate one or more of the drawbacks or limitations in the related art. For example, adaptation of a procedure as a function of a tolerance of procedural steps by an object under examination is provided.

Independent of the grammatical term usage, individuals with male, female or other gender identities are included within the term.

A first aspect of the present embodiments relates to a method for providing a procedural signal. In a first act a), an item of procedural information that includes an item of information about at least one procedural step is received. The at least one procedural step has, for example, been carried out on an object under examination before the beginning of the method. The procedural information further includes an item of information about at least one planned procedural step. In a second act b), a physiological patient parameter of the object under examination, which has been acquired by a sensor unit during and/or subsequent to a procedural step that has been carried out, is received. In a third act c), it is identified based on the patient parameter and/or a change in the patient parameter whether the at least one procedural step has been tolerated by the object under examination. A procedural signal is, for example, provided that, in the negative, includes an item of information for adapting the at least one planned procedural step based on the procedural information and, in the affirmative, includes approval of the at least one planned procedural step.

Receipt of the procedural information may include acquiring and/or reading out a computer-readable data memory (e.g., a database). Alternatively or additionally, the procedural information may be acquired based on a user input on the part of a member of medical operating personnel. The procedural information may include an item of information about at least one procedural step (e.g., a plurality of procedural steps, such as a treatment step and/or examination step that has been carried out, such as completely, on the object under examination before the beginning of the method). The object under examination may include a human or animal patient and/or an examination phantom. The procedural information may, for example, include an item of information about a time sequence of the plurality of procedural steps that have been carried out on the object under examination before the beginning of the method. The procedural information may also include an item of information about at least one planned procedural step (e.g., a plurality of planned procedural steps).

The at least one procedural step may include administration of a medication. Alternatively or additionally, the at least one procedural step may include arranging and/or moving and/or manipulating a medical object (e.g., a medical, such as diagnostic and/or surgical, instrument and/or an implant) on and/or in the object under examination. Alternatively or additionally, the at least one procedural step may include capturing medical image data from the object under examination by a medical imaging device. Alternatively or additionally, the at least one procedural step may include treating at least one treatment region of the object under examination (e.g., performing an ultrasound, brachytherapy, shockwave, and/or irradiation procedure).

The at least one planned procedural step may include at least one procedural step intended for future performance. For example, the at least one planned procedural step may be a planned substep of the at least one procedural step that has been performed before the beginning of the method.

The physiological patient parameter of the object under examination may be provided by the sensor unit. The physiological patient parameter may be considered as monitoring and/or monitor data of the object under examination. The sensor unit may include at least one sensor (e.g., an optical and/or acoustic and/or electromagnetic and/or mechanical sensor, such as a camera and/or a cardiac sensor and/or a respiratory sensor and/or a pulse sensor and/or a temperature sensor) that is configured to acquire (e.g., quantitatively and/or qualitatively) a physiological state of the object under examination. The sensor unit (e.g., the at least one sensor) may, for example, be arranged on the object under examination, in the object under examination, or at a distance from the object under examination. The physiological patient parameter may characterize (e.g., qualitatively and/or quantitatively) the (e.g., instantaneous) physiological state of the object under examination. The physiological patient parameter may have been acquired by the sensor unit (e.g., by at least one sensor) during and/or subsequent to the at least one procedural step that has been carried out. For example, a time profile of the physiological patient parameter may have been acquired by the sensor unit during and/or subsequent to the at least one procedural step acquired that has been carried out.

Act c) may include a comparison of the patient parameter with a specified threshold value. The threshold value may, for example, include a physiological reference value that has been statistically determined or adapted to the object under examination. Alternatively or additionally, the threshold value may be specified based on a user input by the medical operating personnel. Alternatively or additionally, act c) may include identifying a change (e.g., over time) in the patient parameter. For example, a rise or fall in the patient parameter (e.g., a cardiac rate and/or respiratory rate and/or movement) of the object under examination (e.g., over an acquisition period) may be identified as intolerance (e.g., a negative response) of the object under examination to the at least one procedural step. Accordingly, constancy or only slight fluctuation in the patient parameter may be identified as tolerance of the object under examination to the at least one procedural step. Based on the patient parameter and/or the change in the patient parameter, it is possible to identify stress perceptible by the object under examination (e.g., pain and/or discomfort and/or anxiety) and/or physiological stress (e.g., a change in blood flow). In the presence of perceptible and/or physiological stress (e.g., in the event of a stress level, characterized by the patient parameter, of an object under examination exceeding a specified threshold value), it is possible to identify that the at least one procedural step has not been tolerated by the object under examination.

In the affirmative (e.g., on identification of tolerance of the at least one procedural step by the object under examination), it is possible to provide the procedural signal including approval of the at least one planned procedural step (e.g., of the plurality of planned procedural steps or of a first planned procedural step from a sequence of a plurality of planned procedural steps). In the negative (e.g., on identification of an intolerance of the at least one procedural step by the object under examination), the procedural signal including an item of information for adapting the at least one planned procedural step (e.g., the plurality of planned procedural steps or a first planned procedural step from the sequence of a plurality of planned procedural steps) may be provided based on the procedural information. For example, in the negative, provision of the procedural signal may include providing an adaptation signal and/or outputting a workflow notification for automatically adapting the at least one planned procedural step. Adapting the at least one planned procedural step may also include discontinuing and/or stopping the at least one planned procedural step.

Provision of the procedural signal may, for example, include saving on a computer-readable storage medium and/or displaying a graphical representation of the procedural signal by a display unit and/or transfer to a provision unit and/or a remote control unit.

The embodiment may enable approval or adaptation of the at least one planned procedural step as a function of the identified tolerance or intolerance of the at least one procedural step by the object under examination. As a result, it is possible to avoid (e.g., avert; instantaneously) the performance of contraindicated planned procedural steps.

In a further embodiment of the method, acts a) to c) may be performed repeatedly until a termination condition occurs.

The termination condition may specify a number of still remaining planned procedural steps as a maximum number of repeats of acts a) to c). Alternatively or additionally, the termination condition may specify a maximum duration for repeatedly performing acts a) to c) (e.g., as a whole). Alternatively or additionally, identifying an intolerance of the at least one planned procedural step by the object under examination may lead to the termination condition occurring.

The embodiment may enable repeated (e.g., continuous) monitoring of the tolerance of the procedural steps by an object under examination, where performance of the procedural steps is not part of the proposed method.

In a further embodiment of the method, adapting the at least one planned procedural step may include adapting the following element(s): medication; selection of a medical object; movement velocity and/or movement direction and/or positioning and/or trajectory of the medical object; and/or procedural pause.

The at least one planned procedural step may include a specification for a medication (e.g., a dosage and/or rate of administration and/or composition and/or administration sequence of the medication). Adapting the at least one planned procedural step may, for example, include increasing or reducing a dosage and/or rate of administration of the medication and/or adapting the composition and/or sequence of administration of the medication. Alternatively or additionally, the at least one planned procedural step may include a specification for a selection (e.g., identification) of a medical object (e.g., a medical, such as diagnostic and/or surgical, instrument and/or an implant). Adapting the at least one planned procedural step may, for example, include an alternative specification for selecting the medical object. Alternatively or additionally, the at least one planned procedural step may include a specification for a movement velocity and/or movement direction and/or positioning (e.g., spatial position and/or orientation and/or pose) and/or trajectory (e.g., a path) of the medical object (e.g., with regard to the object under examination and/or a medical imaging device and/or a manipulator, such as with regard to the medical operating personnel and/or a remote manipulation unit). Adapting the at least one planned procedural step may, for example, include increasing or decreasing the movement velocity and/or adapting the movement direction and/or positioning and/or trajectory of the medical object. Alternatively or additionally, the at least one planned procedural step may include a specification for a procedural pause (e.g., a time delay until performance of the at least one planned procedural step or a time delay between two successive planned procedural steps). Adapting the at least one planned procedural step may include, for example, reducing or extending the procedural pause.

The embodiment may enable improved adaptation of the at least one planned procedural step.

In a further embodiment of the method, provision of the procedural signal may include outputting a workflow notification.

The workflow notification may be provided by way of a, for example, optical and/or acoustic and/or tactile output unit (e.g., a display unit and/or a loudspeaker). The workflow notification may include the approval or information for adapting the at least one planned procedural parameter. The workflow notification may, for example, take textual and/or spoken and/or symbolic and/or graphical form.

The embodiment may enable comprehensible (e.g., actionable) communication of the procedural signal for approval or adaptation of the at least one planned procedural step to a member of medical operating personnel.

In a further embodiment of the method, the procedural information may include an alternative configuration for the at least one planned procedural step and/or an item of information about at least one alternative planned procedural step. Provision of the procedural signal may, in the negative, include selection of the alternative configuration and/or of the at least one alternative planned procedural step.

The procedural information may include one or more alternative configurations for the at least one planned procedural step (e.g., in each case, one or more configurations for the plurality of planned procedural steps). The procedural information may include an initial configuration (e.g., a standard configuration) for the at least one planned procedural step. The alternative configuration may deviate from the initial configuration in at least one parameter (e.g., the medication, the selection of the medical object, the movement velocity and/or movement direction and/or positioning and/or trajectory of the medical object, and/or the procedural pause). Alternatively or additionally, the procedural information may include an item of information about at least one alternative planned procedural step (e.g., a plurality of alternative planned procedural steps). For example, the procedural information may include an item of information about a sequence of alternative planned procedural steps. The at least one alternative planned procedural step may, for example, be at least partly (e.g., completely) different from the at least one planned procedural step.

In the negative (e.g., on identification of intolerance of the at least one planned procedural step by the object under examination), provision of the procedural signal may include selection of the alternative configuration to the at least one planned procedural step and/or the at least one alternative planned procedural step. For example, provision of the procedural signal may, in the negative, include automatic selection of the alternative configuration to the at least one planned procedural step and/or the at least one alternative planned procedural step. Alternatively or additionally, provision of the procedural signal may, in the negative, include outputting the workflow notification including a specification for selection of the alternative configuration to the at least one planned procedural step and/or the at least one alternative planned procedural step.

The embodiment may enable efficient and at the same time reliable adaptation of the at least one planned procedural step.

In a further embodiment of the proposed method, the at least one procedural step may have been performed by a remotely controlled remote manipulation unit and/or a member of local medical operating personnel, and/or the at least one planned procedural step may be performable by the remotely controlled remote manipulation unit and/or the local medical operating personnel. The procedural signal may, for example, be provided to a remote control unit. As a function of the procedural signal, the remote control unit may adapt the remotely controlled performance of the at least one planned procedural step or approve the remotely controlled performance of the at least one planned procedural step.

The remote manipulation unit (e.g., a telemanipulation unit) may include a medical device that is configured for (e.g., robotic) movement of the object under examination (e.g., a patient positioning apparatus), and/or for robotic movement of the medical object (e.g., a catheter robot and/or a surgical robot), and/or for medical imaging (e.g., a medical imaging device, such as a medical X-ray machine and/or a computed tomography system (CT system) and/or a magnetic resonance tomography system (MM system) and/or an ultrasound scanner and/or a positron emission tomography system (PET system)), and/or for treating the object under examination (e.g., an autoinjector and/or an irradiation system and/or a brachytherapy device and/or a ventilator and/or a histotripsy device). The remote manipulation unit may be configured to perform the at least one planned procedural step (e.g., in interaction with the object under examination). The at least one procedural step may further have been performed by the remote manipulation unit before the beginning of the method.

Alternatively or additionally, the at least one procedural step may have been assisted or carried out before the beginning of the method by the local medical operating personnel (e.g., a physician).

The remote control unit may include a user interface (e.g., an input unit and an output unit, such as a display unit). The procedural signal may be provided to the remote control unit. The user interface (e.g., the output unit) may be configured to output the workflow notification. The input unit may further be configured to acquire a user input from a member of medical operating personnel (e.g., from a member of remote operating personnel). The input unit may, for example, include a keyboard and/or a button and/or a joystick and/or a touchpad and/or a microphone (e.g., for speech acquisition) and/or a camera (e.g., for gesture acquisition). The input unit may be integrated in the display unit (e.g., in the case of a resistive and/or capacitive input display (touchscreen)). The remote control unit may be spatially and/or geographically distant from the remote manipulation unit (e.g., in another room or building). The procedural signal may be provided to the remote control unit via telecommunications (e.g., via a secure network connection).

As a function of the procedural signal (e.g., on identification of a tolerance of the at least one procedural step by the object under examination), the remote control unit may approve remotely controlled performance of the at least one planned procedural step. Alternatively (e.g., on identification of an intolerance of the at least one procedural step by the object under examination), the remote control unit may adapt the remotely controlled performance of the at least one planned procedural step. For example, the remote control unit may adapt (e.g., extend or limit) degrees of freedom for remote control of the remote manipulation unit as a function of the procedural signal. Adapting the at least one planned procedural step may also include interrupting (e.g., pausing) or stopping the procedure.

The remote manipulation unit may be remotely controllable by the remote control unit (e.g., based on a control signal provided by the remote control unit). The remote control unit may, for example, be configured to automatically control the remote manipulation unit to perform the at least one planned procedural step. The, for example, automatic performance of the at least one planned procedural step may be monitored by the remote operating personnel and/or the local operating personnel.

Alternatively or additionally, the remote control unit may be configured to remotely control the at least one planned procedural step based on the user input. For example, the remote control unit may remotely control the remote manipulation unit based on the user input (e.g., via the control signal). Alternatively or additionally, the remote control unit may provide a further workflow notification (e.g., an instruction) for performing the at least one planned procedural step and/or for assisting with the performance of the at least one planned procedural step to the local operating personnel (e.g., via the control signal).

The embodiment may prevent instructions (e.g., treatment instructions) that are not performable by the local operating personnel and/or the remote manipulation unit, are medically contraindicated, and/or are not tolerable by the object under examination from being provided (e.g., repeatedly) to local operating personnel and/or the remote manipulation unit due to lack of information on the part of the remote operating personnel.

In a further embodiment of the method, the remote manipulation unit may be configured to robotically move a medical object. As a function of the procedural signal, the remote control unit may, for example, approve, adapt, or stop the robotic movement of the medical object or specify a safety movement as the robotic movement.

The remote manipulation unit may include a robotic movement apparatus (e.g., a surgical robot and/or a catheter robot) for robotically moving the medical object. The movement apparatus may be configured to position (e.g., orient) and/or move (e.g., translate and/or rotate and/or deform) and/or control the medical object. As a function of the procedural signal (e.g., on identification of a tolerance of the at least one procedural step by the object under examination), the remote control unit may approve the robotic movement of the medical object by the remote manipulation unit. Alternatively, for example, on identification of an intolerance of the at least one procedural step by the object under examination, the remote control unit may adapt (e.g., slow and/or accelerate and/or redirect) or stop the robotic movement of the medical object by the remote manipulation unit, or specify a safety movement as the robotic movement. The safety movement may, for example, include a movement of the medical object into a stable position and/or a backward movement of the medical object that is a movement of the medical object in the opposite direction to a movement in the at least one procedural step.

The embodiment may enable efficient and reliable monitoring and adaptation of the robotic movement of the medical object by the remote manipulation unit.

In a further embodiment of the method, the remote manipulation unit may be configured to administer a medication. As a function of the procedural signal, the remote control unit may adapt a rate of administration and/or dose and/or composition of the medication and/or stop or approve administration of the medication.

The remote manipulation unit may include an autoinjector that is configured to administer (e.g., inject) the medication (e.g., an anesthetic and/or contrast agent). As a function of the procedural signal (e.g., on identification of a tolerance of the at least one procedural step by the object under examination), the remote control unit may approve administration of the medication by the remote manipulation unit (e.g., the autoinjector). Alternatively (e.g., on identification of an intolerance of the at least one procedural step by the object under examination), the remote control unit may adapt the rate of administration and/or dose and/or composition of the medication and/or adapt administration of the medication by the remote manipulation unit (e.g., the autoinjector).

The embodiment may enable efficient and reliable monitoring and adaptation of the administration of the medication by the remote manipulation unit.

In a further embodiment of the method, the patient parameter may characterize physiological stress and/or a cardiac rate and/or respiratory rate and/or blood pressure and/or pain level and/or a, for example, uncontrolled movement and/or facial expression and/or a tremor of the object under examination.

The patient parameter may, for example, directly characterize a physiological parameter of the object under examination (e.g., the cardiac rate and/or respiratory rate and/or blood pressure). Alternatively or additionally, the patient parameter may characterize the physiological stress and/or pain level and/or movement and/or facial expression and/or tremor of the object under examination (e.g., indirectly) based on the at least one detectable physiological parameter (e.g., a plurality of detectable physiological parameters) of the object under examination. The at least one physiological parameter may, for example, include the cardiac rate (e.g., a pulse) and/or a respiratory rate and/or a movement rate and/or a movement amplitude and/or a skin conductivity value and/or a body temperature and/or a blood pressure and/or a change in facial expression of and/or volume of sound from the object under examination.

The embodiment may enable improved monitoring of the tolerance of the at least one procedural step by the object under examination.

In a further embodiment of the method, a preprocedural data set of the object under examination, including an item of information about at least one contraindication, may be received. In act c), it may, for example, additionally be identified based on preprocedural data set whether the at least one planned procedural step is tolerable by the object under examination.

The preprocedural data set may include medical history data of the object under examination (e.g., an item of information about age and/or gender and/or weight and/or size and/or preexisting diseases of the object under examination). Alternatively or additionally, the preprocedural data set may include an item of information about at least one procedure that has been carried out on the object under examination before the beginning of the method (e.g., an item of information about tolerance or intolerance of the procedure, such as of procedural steps of the procedure, by the object under examination). The preprocedural data set may also include measurement data (e.g., preprocedurally acquired physiological parameters and/or medical image data) of the object under examination. The preprocedural data set may include an item of information about at least one contraindication (e.g., a plurality of contraindications). The information about at least one contraindication may relate, for example, to least one planned procedural step and/or a configuration of at least one planned procedural step. Act c) may, for example, include a comparison of the at least one contraindication (e.g., of the at least one contraindicated planned procedural step and/or of the at least one contraindicated configuration of the at least one planned procedural step) with the at least one planned procedural step. Based on the comparison, it may also be identified whether the at least one planned procedural step is (e.g., will be) tolerable by the object under examination.

A second aspect of the present embodiments relates to a system including a sensor unit and a provision unit that is configured to perform a method for providing a procedural signal.

The advantages of the proposed system substantially correspond to the advantages of the proposed method for providing a procedural signal. Features, advantages, or alternative embodiments mentioned in this connection are likewise also applicable to the other claimed subjects and vice versa.

In a further embodiment of the proposed system, the system may also include a remotely controlled remote manipulation unit and a remote control unit for remotely controlling the remote manipulation unit. The remote manipulation unit may, for example, be configured to perform the at least one procedural step and/or the at least one planned procedural step. The remote control unit may be configured to receive the procedural signal. As a function of the procedural signal, the remote control unit may also adapt remote control of the remote manipulation unit for performing the at least one planned procedural step or approve performance of the at least one planned procedural step.

In a further embodiment of the proposed system, the remote manipulation unit may be configured to robotically move a medical object. As a function of the procedural signal, the remote control unit may, for example, be configured to approve, adapt, or stop the robotic movement of the medical object or to specify a safety movement as the robotic movement.

The remote manipulation unit may be configured to receive a proximal portion of the medical object. The remote manipulation unit may, for example, be configured to hold and/or move (e.g., translate and/or rotate) the proximal portion of the medical object by transferring a force. The remote manipulation unit may also be configured to position (e.g., spatially arrange and/or orient) and/or to move (e.g., translate and/or rotate and/or deform) a distal portion of the medical object, for example, by transferring a force onto the proximal portion of the medical object. In one operating state of the system, the distal portion may, for example, be arranged on or in the object under examination (e.g., a hollow organ and/or tissue of the object under examination).

In a further embodiment of the proposed system, the remote manipulation unit may be configured to administer a medication. As a function of the procedural signal, the remote control unit may, for example, be configured to adapt a rate of administration and/or dose and/or composition of the medication and/or to approve or stop administration of the medication.

A third aspect of the present embodiments relates to a computer program product with a computer program that is directly loadable into a memory of a provision unit, having program parts for performing all the acts of the proposed method for providing a procedural signal when the program parts are executed by the provision unit. The computer program product may in this respect include software with source code that has yet to be compiled and linked or has merely to be interpreted, or executable software code that has merely to be loaded into the provision unit for execution. The computer program product may quickly, identically repeatably, and robustly perform the method for providing a procedural signal via a provision unit. The computer program product is configured such that the computer program may perform the method acts according to the present embodiments via the provision unit. In addition to the computer program, such a computer program product may optionally include additional elements such as, for example, documentation and/or additional components, as well as hardware components, such as, for example, hardware keys (e.g., dongles etc.) for using the software.

The advantages of the proposed computer program product substantially correspond to the advantages of the proposed method for providing a procedural signal. Features, advantages, or alternative embodiments mentioned in this connection are likewise also applicable to the other claimed subjects and vice versa.

The present embodiments may further be based on a computer-readable storage medium (e.g., a non-transitory computer-readable storage medium) and/or electronically readable data storage medium on which program parts readable and executable by a provision unit are stored in order to perform all the acts of the method for providing a procedural signal when the program parts are executed by the provision unit. A largely software-based embodiment has the advantage that provision units that are already in service may also straightforwardly be retrofitted to operate in the manner according to the present embodiments by a software update.

BRIEF DESCRIPTION OF THE DRAWINGS

Examples of embodiments of the invention are shown in the drawings and described in greater detail below. Same reference signs are used for same features in different figures. In the figures.

DETAILED DESCRIPTION

Figure 1:
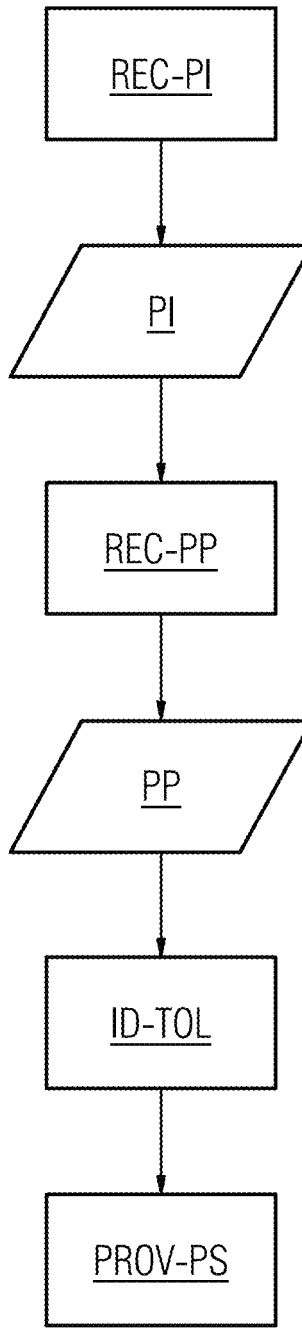
FIGS. 1 to 3 show schematic representation of various embodiments of a method for providing a procedural signal.

FIG. 1 is a diagrammatic representation of an embodiment of a method for providing a procedural signal PROV-PS. In a first act a), an item of procedural information PI that includes an item of information about at least one procedural step may be received REC-PI. The at least one procedural step may, for example, have been carried out on an object under examination before the beginning of the method (e.g., by a remotely controlled remote manipulation unit and/or a member of local medical operating personnel). The procedural information PI may further include an item of information about at least one planned procedural step. For example, the procedural information PI may include an alternative configuration to the at least one planned procedural step and/or an item of information about at least one alternative procedural step. In a second act b), a physiological patient parameter PP of the object under examination, which has been acquired by a sensor unit during and/or subsequent to the procedural step that has been carried out, is received REC-PP. The patient parameter PP may characterize physiological stress and/or a cardiac rate and/or a respiratory rate and/or a blood pressure and/or a pain level and/or a movement and/or facial expression and/or a tremor of the object under examination. In a third act c), it may be identified ID-TOL, based on the patient parameter PP and/or a change in the patient parameter PP, whether the at least one procedural step has been tolerated by the object under examination. A procedural signal may further be provided PROV-PS. Based on the identification ID-TOL, in the negative, the procedural signal includes an item of information for adapting the at least one planned procedural step based on the procedural information PI, and, in the affirmative, the procedural signal includes approval of the at least one planned procedural step. Provision of the procedural signal PROV-PS may further, in the negative, include selection of the alternative configuration and/or of the at least one alternative planned procedural step.

In the context of the proposed method, tolerance of the at least one procedural step by the object under examination and/or the approval and/or adaptation of the at least one planned procedural step may be documented (e.g., as a contraindication) for subsequent planned procedural steps. Documentation may, for example, include documentation of the information available for the decision (e.g., the patient parameter and the procedural information).

Adapting the at least one planned procedural step may include adapting medication, adapting selection of a medical object, adapting movement velocity and/or movement direction and/or positioning and/or trajectory of the medical object, and/or adapting procedural pause.

Provision of the procedural signal PROV-PS may include outputting a workflow notification. The at least one planned procedural step may be performable by a remotely controlled remote manipulation unit and/or a member of local medical operating personnel. The procedural signal may, for example, be provided PROV-PS to a remote control unit. As a function of the procedural signal, the remote control unit may adapt the remotely controlled performance of the at least one planned procedural step or approve the remotely controlled performance of the at least one planned procedural step. For example, the remote manipulation unit may be configured to robotically move a medical object. As a function of the procedural signal, the remote control unit may, for example, approve, adapt, or stop the robotic movement of the medical object, or specify a safety movement as the robotic movement. Alternatively or additionally, the remote manipulation unit may be configured to administer a medication. As a function of the procedural signal, the remote control unit may adapt a rate of administration and/or dose and/or composition of the medication and/or stop or approve administration of the medication.

Figure 2:
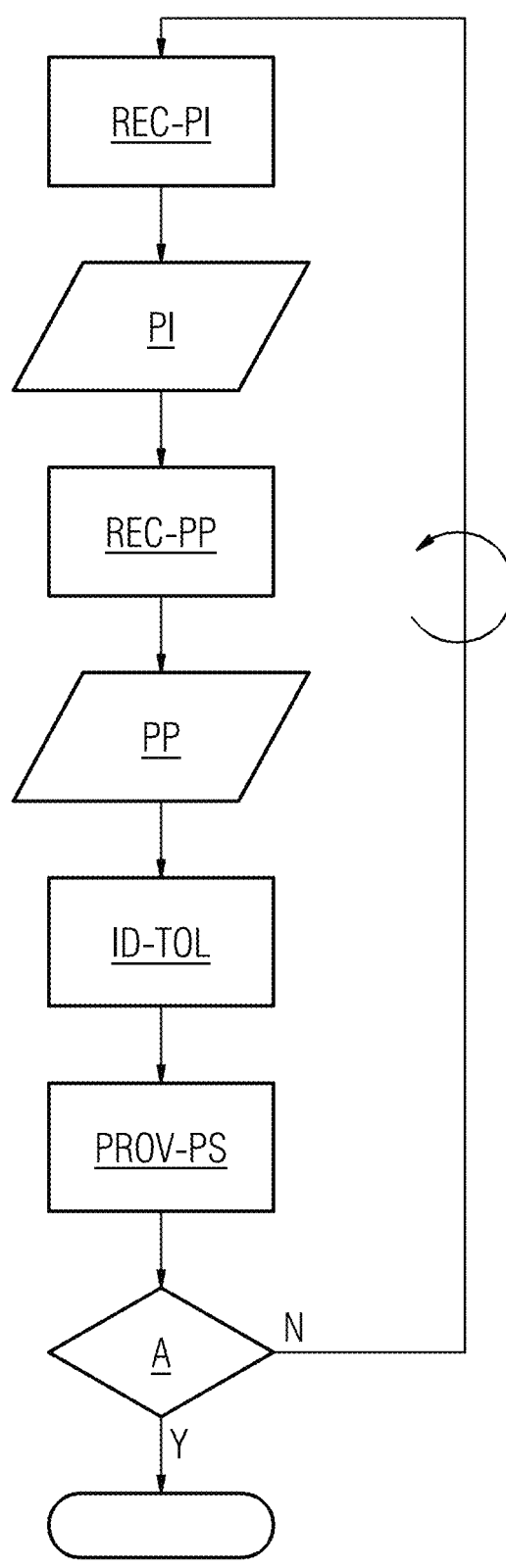

FIG. 2 is a diagrammatic representation of a further embodiment of the method for providing a procedural signal PROV-PS. Acts a) to c) may, for example, be performed repeatedly until a termination condition A occurs Y.

Figure 3:
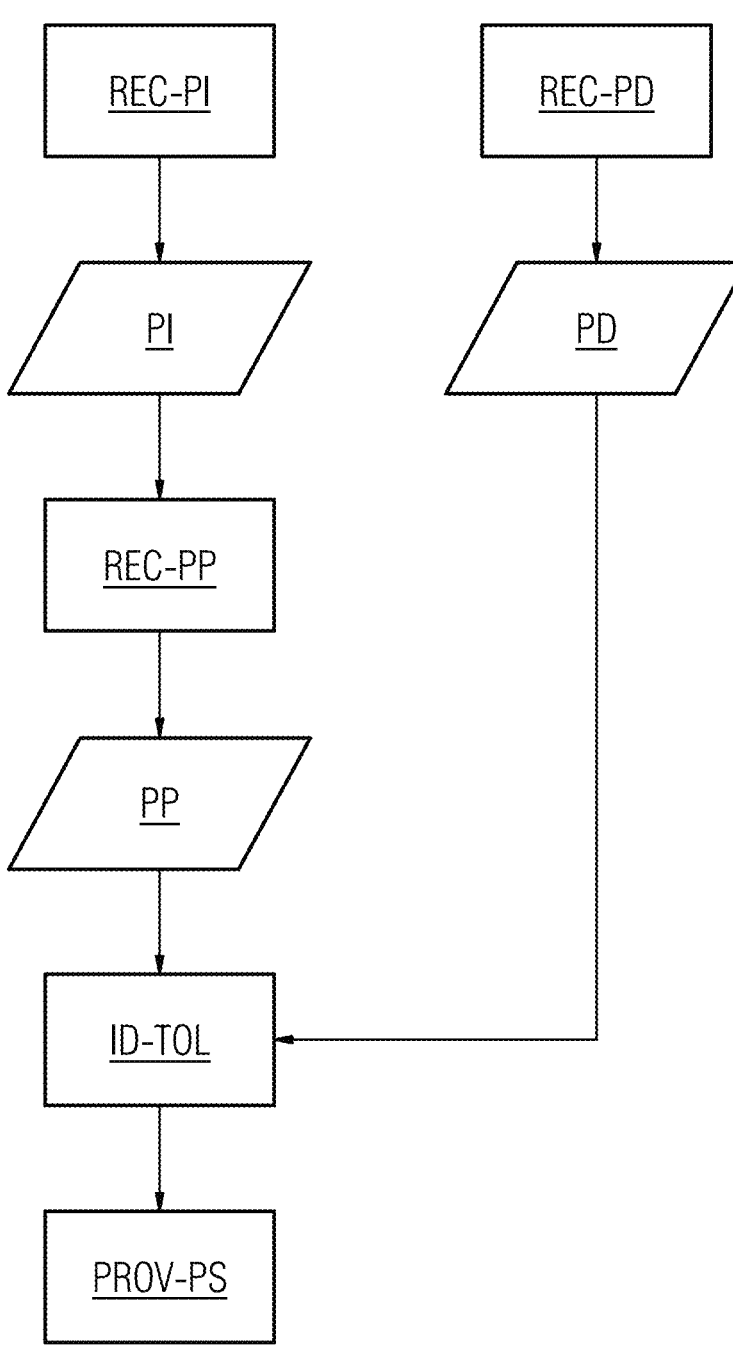

FIG. 3 is a diagrammatic representation of a further embodiment of the method for providing a procedural signal PROV-PS. A preprocedural data set PD of the object under examination, including an item of information about at least one contraindication, may, for example, be received REC-PD. In act c), it may, for example, additionally be identified, based on the preprocedural data set PD, whether the at least one planned procedural step is tolerable by the object under examination.

Figure 4:
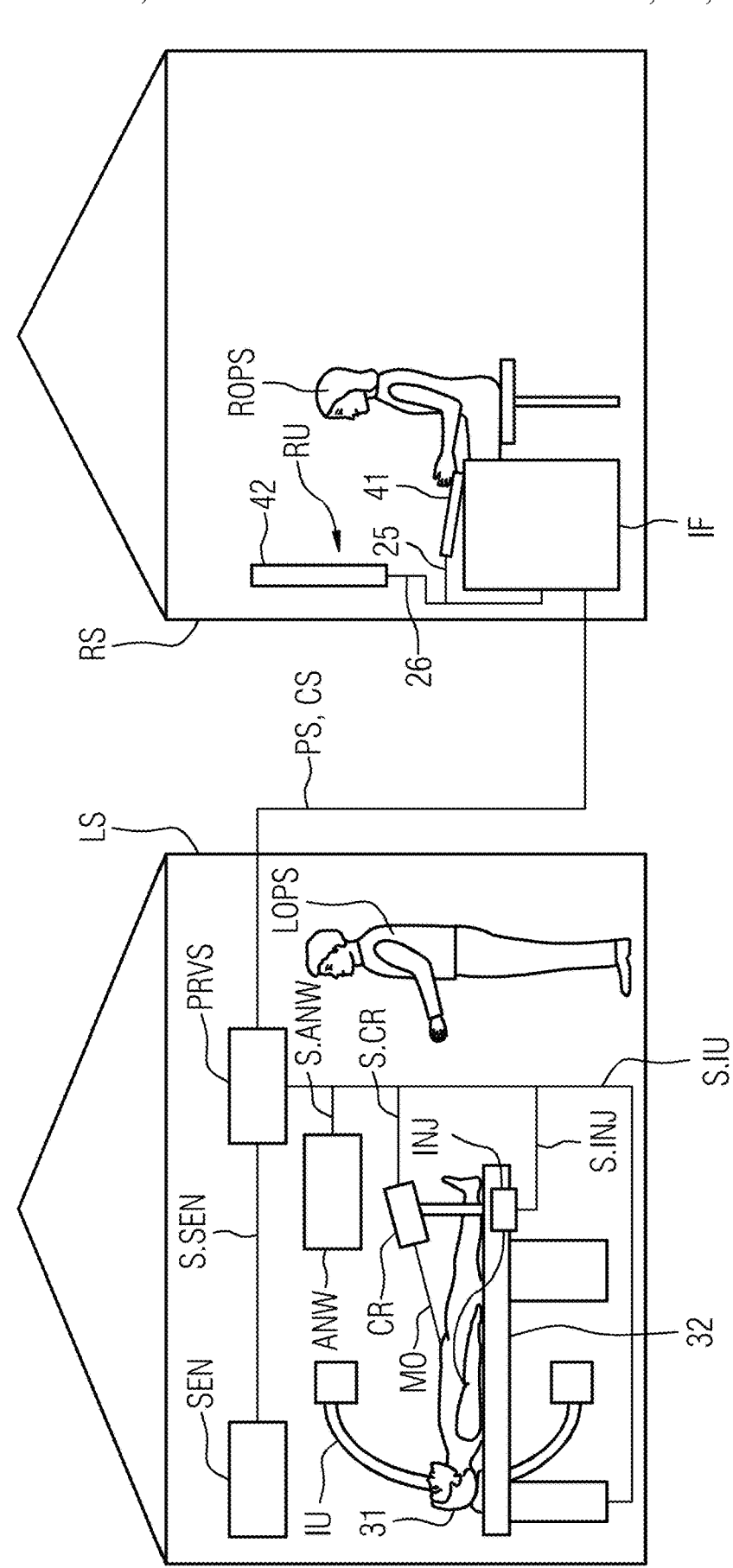
FIG. 4 shows a schematic representation of an embodiment of a system.

FIG. 4 shows a schematic representation of an embodiment of a system. The system may, for example, include a sensor unit SEN, a provision unit PRVS (e.g., including a processor), a remote manipulation unit, and a remote control unit RU for remotely controlling the remote manipulation unit.

The sensor unit SEN may include at least one sensor (e.g., an optical and/or acoustic and/or electromagnetic and/or mechanical sensor, such as a camera, and/or a cardiac sensor and/or a respiratory sensor and/or a pulse sensor and/or a temperature sensor) that is configured to acquire (e.g., quantitatively and/or qualitatively) a physiological state of the object under examination 31 arranged on a patient positioning apparatus 32. The sensor unit SEN (e.g., the at least one sensor) may, for example, be arranged on the object under examination 31, in the object under examination 31, or at a distance from the object under examination 31 (as shown by way of example in FIG. 4). As a function of the acquired physiological state of the object under examination 31, the sensor unit SEN may provide a signal S.SEN to the provision unit PRVS.

The provision unit PRVS may be configured to receive REC-PP the physiological patient parameter PP based on the signal S. SEN.

The remote control unit RU may include a user interface (e.g., an input unit 41 and an output unit, such as a display unit 42). The provision unit PRVS may provide the procedural signal PS to the remote control unit RU (e.g., an interface IF of the remote control unit RU). The procedural signal PS may be provided to the remote control unit RU (e.g., the interface IF) via telecommunications (e.g., via a secure network connection).

The input unit 41 may further be configured to acquire a user input from a member of remote medical operating personnel ROPS. The input unit 41 may, for example, include a keyboard and/or a button and/or a joystick and/or a touchpad and/or a microphone, for example, for speech acquisition, and/or a camera, for example, for gesture acquisition. The input unit 41 may be integrated in the display unit 42 (e.g., in the case of a resistive and/or capacitive input display). The remote control unit RU may, as illustrated in FIG. 4, be arranged spatially and geographically distant from the remote manipulation unit. For example, the object under examination 31, the sensor unit SEN, and the remote manipulation unit may be arranged in a local treatment room LS, and the remote control unit RU and the remote operating personnel ROPS may be arranged in a remote operating room RS. Additionally, the procedure in the local treatment room LS may be monitored, assisted, and/or at least in part carried out by a member of local medical operating personnel LOPS.

A medical imaging device (e.g., a medical C-arm X-ray machine IU) may be arranged in the local treatment room LS for capturing medical image data from the object under examination 31. The C-arm X-ray machine IU may be communicatively linked with the provision unit PRVS via a signal S.IU. The C-arm X-ray machine IU (e.g., capture of the image data and/or movement of the C-arm X-ray machine IU) may be remotely controllable by a control signal CS from the remote control unit RU (e.g., as a function of a user input from the remote medical operating personnel ROPS). Based on the signal S.IU, the provision unit PRVS may receive the medical image data and provide the medical image data via the procedural signal PS to the remote control unit RU. The display unit 42 may be configured to output a graphical representation of the workflow notification and/or the patient parameter PP and/or the medical image data. The interface IF may to this end send a signal 26 to the display unit 42.

The remote control unit RU may be configured to receive the procedural signal PS. As a function of the procedural signal PS (e.g., on identification of tolerance of the at least one procedural step by the object under examination 31), the remote control unit RU may approve remotely controlled performance of the at least one planned procedural step. Alternatively, for example, on identification of an intolerance of the at least one procedural step by the object under examination 31, the remote control unit RU may adapt the remotely controlled performance of the at least one planned procedural step. For example, the remote control unit RU may adapt (e.g., extend or limit) degrees of freedom for remote control of the remote manipulation unit as a function of the procedural signal PS. Adapting the at least one planned procedural step may also include interrupting (e.g., pausing) or stopping the procedure.

The remote manipulation unit may be remotely controllable via the remote control unit RU (e.g., based on the control signal CS provided by the remote control unit RU). The remote control unit RU may, for example, be configured to control the remote manipulation unit to perform the at least one planned procedural step automatically. The, for example, automatic performance of the at least one planned procedural step may further be monitored by the remote operating personnel ROPS and/or the local operating personnel LOPS.

Alternatively or additionally, the remote control unit RU may be configured to remotely control the at least one planned procedural step based on the user input. For example, the remote control unit RU may remotely control the remote manipulation unit based on the user input, for example, via the control signal CS. Alternatively or additionally, the remote control unit RU may provide a further workflow notification (e.g., an instruction) for performing the at least one planned procedural step and/or for assisting with the performance of the at least one planned procedural step to the local operating personnel LOPS (e.g., by outputting the control signal CS via an output unit ANW). The output unit ANW may, for example, include a loudspeaker and/or a further display unit. The output unit may further be communicatively linked with the provision unit PRVS via a signal S.ANW.

The remote manipulation unit may include a movement apparatus CR (e.g., a catheter robot) and an autoinjector INJ. The movement apparatus CR may be communicatively linked with the provision unit via a signal S.CR and the autoinjector INJ via a signal S.INJ. The movement apparatus CR may be configured to robotically move a medical object MO, (e.g., a catheter and/or surgical instrument that, in an operating state of the system, is arranged at least in part in the object under examination 31). As a function of the procedural signal PS, the remote control unit RU may further be configured (e.g., via the control signal CS) to approve, adapt, or stop the robotic movement of the medical object MO or to specify a safety movement as the robotic movement.

The autoinjector INJ may be configured to administer a medication (e.g., a contrast agent). As a function of the procedural signal PS, the remote control unit RU may, for example, be configured (e.g., via the control signal CS) to adapt a rate of administration and/or dose and/or composition of the medication and/or to approve or stop administration of the medication. The remote manipulation unit (e.g., the movement apparatus CR and the autoinjector INJ) may be configured to perform the at least one procedural step and/or the at least one planned procedural step.

The schematic representations contained in the described figures do not depict any scale or size ratios.

In the context of the present application, the expression "on the basis of" may, for example, be understood to be "using". For example, wording according to which a first feature is generated (e.g., established, determined, etc.) based on a second feature does not rule out the possibility of the first feature being generated (e.g., established, determined, etc.) based on a third feature.

The method described above in detail and the depicted apparatuses are merely embodiments that may be modified in the most varied manner by a person skilled in the art without departing from the scope of the invention. Further, use of the indefinite article "a" does not rule out the possibility of a plurality of the features in question also being present. Likewise, the terms "unit" and "element" do not rule out the possibility of the components in question consisting of a plurality of interacting sub-components that may optionally also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for providing a procedural signal, the method comprising:

receiving, by a processor, an item of procedural information, the item of procedural information including an item of information about at least one procedural step that has been carried out on an object under examination before a beginning of the method, and including an item of information about at least one planned procedural step, the at least one procedural step that has been carried out including administration of a medicine, arranging, moving, manipulating, or any combination thereof of a medical object on, in, or on and in the object under examination, capturing medical image data from the object under examination by a medical imaging device, treating at least one treatment region of the object under examination by a medical treatment device, or any combination thereof;

receiving, by the processor, a physiological patient parameter from the object under examination, which has been acquired by at least one sensor during, subsequent to, or during and subsequent to the at least one procedural step that has been carried out;

identifying, by the processor, based on the physiological patient parameter, a change in the physiological patient parameter, or the physiological patient parameter and the change in the physiological patient parameter, whether the at least one procedural step that has been carried out has been tolerated by the object under examination;

based on the identifying, determining, by the processor, that the at least one procedural step that has been carried out has not been tolerated by the objected under examination;

based on the determining, providing the procedural signal, which includes an item of information for adapting the at least one planned procedural step based on the procedural information; and executing, by a manipulator in communication with the processor, the adapted at least one planned procedural step based on the provided procedural signal using a medical object.

2. The method of claim 1, wherein the receiving of the item of procedural information, the receiving of the physiological patient parameter, and the identifying are performed repeatedly until a termination condition occurs.

3. The method of claim 1, wherein adapting the at least one planned procedural step comprises adapting:

medication;

selection of the medical object;

movement velocity, movement direction, positioning, trajectory, or any combination thereof of the medical object;

procedural pause; or any combination thereof.

4. The method of claim 1, wherein providing the procedural signal comprises outputting a workflow notification.

5. The method of claim 1, wherein the procedural information includes an alternative configuration to the at least one planned procedural step, an item of information about at least one alternative planned procedural step, or a combination thereof, and wherein providing the procedural signal, in the negative, comprises selecting the alternative configuration, the at least one alternative planned procedural step, or the alternative configuration and the at least one alternative planned procedural step.

6. The method of claim 1, wherein:

the manipulator is a remotely controlled manipulator, the at least one procedural step has been performed by the remotely controlled manipulator, a member of local medical operating personnel, or a combination thereof;

the at least one planned procedural step is performable by the remotely controlled manipulator, the member of local medical operating personnel, or a combination thereof; or a combination thereof, wherein providing the procedural signal comprises providing the procedural signal to a remote controller, and wherein the method further comprises adapting, by the remote controller, a remotely controlled performance of the at least one planned procedural step or approving, by the remote controller, the remotely controlled performance of the at least one planned procedural step as a function of the procedural signal.

7. The method of claim 6, wherein the remotely controlled manipulator is configured to robotically move the medical object, and wherein the method further comprises approving, adapting, or stopping, by the remote controller, the robotic movement of the medical object or specifying, by the remote controller, a safety movement as the robotic movement as a function of the procedural signal.

8. The method of claim 6, wherein the remotely controlled manipulator is configured to administer a medication, and wherein the method further comprises adjusting, by the remote controller, a rate of administration of the medication, dose of the medication, composition of the medication, or any combination thereof, stopping or approving, by the remote controller, administration of the medication, or a combination thereof as a function of the procedural signal.

9. The method of claim 1, wherein the physiological patient parameter characterizes physiological stress, a cardiac rate, a respiratory rate, a blood pressure, a pain level, a movement, facial expression, a tremor, or any combination thereof of the object under examination.

10. The method of claim 1, further comprising receiving a preprocedural data set of the object under examination, the preprocedural data set including an item of information about at least one contraindication, and wherein the identifying comprises identifying, based on the preprocedural data set, whether the at least one planned procedural step is tolerable by the object under examination.

11. A system comprising:

at least one sensor; and a processor configured to provide a procedural signal, the processor being configured to provide the procedural signal comprising the processor being configured to:

receive an item of procedural information, the item of procedural information including an item of information about at least one procedural step that has been carried out on an object under examination before a beginning of the provision of the procedural signal, and including an item of information about at least one planned procedural step, the at least one procedural step that has been carried out including administration of a medicine, arrangement, movement, manipulation, or any combination thereof of a medical object on, in, or on and in the object under examination, capture of medical image data from the object under examination by a medical imaging device, treating at least one treatment region of the object under examination by a medical treatment device, or any combination thereof;

receive a physiological patient parameter from the object under examination, which has been acquired by the at least one sensor during, subsequent to, or during and subsequent to the at least one procedural step that has been carried out;

identify, based on the physiological patient parameter, a change in the physiological patient parameter, or the physiological patient parameter and the change in the physiological patient parameter, whether the at least one procedural step that has been carried out has been tolerated by the object under examination;

based on the identification, determine that the at least one procedural step that has been carried out has not been tolerated by the objected under examination;

based on the determination, provide the procedural signal, which, in the negative, includes an item of information for adapting the at least one planned procedural step based on the procedural information; and execute, by a manipulator in communication with the processor, the adapted at least one planned procedural step based on the provided procedural signal using a medical object, the remotely controlled manipulator being remote relative to the processor.

12. The system of claim 11, further comprising:

the manipulator, the manipulator being remote relative to the processor; and a remote controller configured to remotely control the remote manipulator, wherein the remote manipulator is configured to perform the at least one procedural step, the at least one planned procedural step, or the at least one procedural step and the at least one planned procedural step, wherein the remote controller is configured to receive the procedural signal, and wherein, as a function of the procedural signal, the remote controller is configured to:

adapt the remote control of the remote manipulator for performing the at least one planned procedural step; or approve performance of the at least one planned procedural step.

13. The system of claim 12, wherein the remote manipulator is configured to robotically move the medical object, and
   wherein, as a function of the procedural signal, the remote controller is configured to:
      approve, adapt, or stop the robotic movement of the medical object; or
      specify a safety movement as the robotic movement.

14. The system of claim 12, wherein the remote manipulator is configured to administer a medication, and
   wherein, as a function of the procedural signal, the remote controller is configured to:
      adapt a rate of administration of the medication, dose of the medication, composition of the medication, or any combination thereof;
      approve or stop administration of the medication; or
      a combination thereof.

15. A non-transitory computer-readable storage medium that stores instructions executable by one or more processors to provide a procedural signal, the instructions comprising:
   receiving, by a processor of the one or more processors, an item of procedural information, the item of procedural information including an item of information about at least one procedural step that has been carried out on an object under examination before a beginning of the method, and including an item of information about at least one planned procedural step, the at least one procedural step that has been carried out including administration of a medicine, arranging, moving, manipulating, or any combination thereof of a medical object on, in, or on and in the object under examination, capturing medical image data from the object under examination by a medical imaging device, treating at least one treatment region of the object under examination by a medical treatment device, or any combination thereof;
   receiving a physiological patient parameter from the object under examination, which has been acquired by at least one sensor during, subsequent to, or during and subsequent to the at least one procedural step that has been carried out;
identifying, based on the physiological patient parameter, a change in the physiological patient parameter, or the physiological patient parameter and the change in the physiological patient parameter, whether the at least one procedural step that has been carried out has been tolerated by the object under examination;
based on the identifying, determining, by the processor, that the at least one procedural step that has been carried out has not been tolerated by the objected under examination;
based on the determining, providing the procedural signal, which includes an item of information for adapting the at least one planned procedural step based on the procedural information; and
executing, by a manipulator in communication with the processor, the adapted at least one planned procedural step based on the provided procedural signal using a medical object.

16. The non-transitory computer-readable storage medium of claim 15, wherein the receiving of the item of procedural information, the receiving of the physiological patient parameter, and the identifying are performed repeatedly until a termination condition occurs.

17. The non-transitory computer-readable storage medium of claim 15, wherein adapting the at least one planned procedural step comprises adapting:
   medication;
   selection of the medical object;
   movement velocity, movement direction, positioning, trajectory, or any combination thereof of the medical object;
   procedural pause; or
   any combination thereof.

18. The non-transitory computer-readable storage medium of claim 15, wherein providing the procedural signal comprises outputting a workflow notification.

* * * * *